(12) United States Patent
Song-Ping

(10) Patent No.: US 6,670,329 B2
(45) Date of Patent: Dec. 30, 2003

(54) *SELENOCOSMIA HUWENA* TOXIN AND ANALGESIC USES THEREOF

(75) Inventor: Liang Song-Ping, Hunan (CN)

(73) Assignee: Xiamen Bioway Biotech Co., Ltd., Xiamen (CN)

( * ) Notice: Subject to any disclaimer, the term of this patent is extended or adjusted under 35 U.S.C. 154(b) by 0 days.

(21) Appl. No.: 09/782,704

(22) Filed: Feb. 13, 2001

(65) Prior Publication Data

US 2003/0013647 A1 Jan. 16, 2003

(30) Foreign Application Priority Data

Apr. 11, 2000 (CN) ........................................ 00104254 A

(51) Int. Cl.$^7$ .......................... A61K 38/00; A61K 45/00
(52) U.S. Cl. .............................. 514/12; 514/2; 530/350; 435/69.1; 435/320.1; 435/440; 435/94; 435/7.1; 435/7.2; 536/23.1; 424/9.1; 424/278.1
(58) Field of Search ........................ 514/2, 12; 530/350, 530/412; 435/7.1, 7.2, 69.1, 320.1, 440, 94; 424/9.1, 278.1; 604/19; 536/23.1

(56) References Cited

U.S. PATENT DOCUMENTS 6,156,726 A    12/2000   Newcomb et al.

OTHER PUBLICATIONS

Li et al., "Cloning and Functional Expression of a Synthetic Gene Enclloding Huwentoxin–I, a Neurotoxin from the Chinese Bird Spider", Toxicon 38:153–162, 2000, XP–001018420.

GenBank Accession No. AF157504; Li et al, Submitted Jun. 8, 1999.

GenBank Accession No. AF157504_1; Li et al, Submitted Jun. 8, 1999.

Liang et al., "The presynaptic activity of huwentoxin–I, a neurotoxin from the venom of the Chinese bird spider *Selenocosmia huwena*," *Toxicon*, 38:1237–1246 (2000).

Peng et al., "The effect of Huwentoxin–I on $Ca^{2+}$ channels in differentiated NG108–15 cells, a patch–clamp study," *Toxicon* 00:1–8 (2000).

Songping et al., "Solid–phase synthesis of huwentoxin–I and its structure and bioactivity analysis*," *Science in China*, 40:5 (1997).

*Primary Examiner*—Karen Cochran Carlson
*Assistant Examiner*—Samuel W. Liu
(74) *Attorney, Agent, or Firm*—Fish & Richardson P.C.

(57) ABSTRACT

Disclosed is a analgesic composition containing the purified HWAP-I polypeptide of the Chinese bird spider, *Selenocosmia Huwena*.

18 Claims, No Drawings

SEQUENCE LISTING

<160> NUMBER OF SEQ ID NOS: 5

<210> SEQ ID NO 1
<211> LENGTH: 33
<212> TYPE: PRT
<213> ORGANISM: Selenocosmia huwena

<400> SEQUENCE: 1

Ala Cys Lys Gly Val Phe Asp Ala Cys Thr Pro Gly Lys Asn Glu Cys
 1               5                  10                  15

Cys Pro Asn Arg Val Cys Ser Asp Lys His Lys Trp Cys Lys Trp Lys
            20                  25                  30

Leu

<210> SEQ ID NO 2
<211> LENGTH: 96
<212> TYPE: DNA
<213> ORGANISM: Selenocosmia huwena

<400> SEQUENCE: 2
gcatgcaaag gggtcttcga tgcatgcaca cctggaaaga atgagtgctg tccaaaccgt     60
gtttgtagta aacacaagtg gtgcaaatgg aagctg                              96

<210> SEQ ID NO 3
<211> LENGTH: 99
<212> TYPE: DNA
<213> ORGANISM: Artificial Sequence
<220> FEATURE:
<223> OTHER INFORMATION: Synthetic oligonucleotide

<400> SEQUENCE: 3
gcttgcaaag gtgttttcga cgcttgcacc ccgggtaaaa acgagtgctg cccgaaccgt     60
gtttgctctg acaaacataa atggtgcaaa tggaaactg                           99

<210> SEQ ID NO 4
<211> LENGTH: 108
<212> TYPE: DNA
<213> ORGANISM: Artificial Sequence
<220> FEATURE:
<223> OTHER INFORMATION: Synthetic oligonucleotide

<400> SEQUENCE: 4
gatccgcttg caaaggtgtt ttcgacgctt gcaccccggg taaaaacgag tgctgcccga     60
accgtgtttg ctctgacaaa cataaatggt gcaaatggaa actgtgag                 108

<210> SEQ ID NO 5
<211> LENGTH: 108
<212> TYPE: DNA
<213> ORGANISM: Artificial Sequence
<220> FEATURE:
<223> OTHER INFORMATION: Synthetic oligonucleotide

<400> SEQUENCE: 5
aattctcaca gtttccattt gcaccattta tgtttgtcag cgcaaacacg gttcgggcag    60
cactcgtttt tacccggggt gcaagcgtcg aaaacacctt tgcaagcg                 108

*SELENOCOSMIA HUWENA* TOXIN AND ANALGESIC USES THEREOF

CROSS-REFERENCE TO RELATED APPLICATIONS

Pursuant to 35 U.S.C. 35 §119, this application claims priority from China application No. 00104254.8, filed Apr. 11, 2000.

BACKGROUND

Analgesics and other medicines that relieve pain are critical therapeutics that vastly improve the quality of life of sufferers and their caretakers. Analgesics not only relieve pain, but also the dread, tension, anxiety and unpleasant perceptions inflicted by acute pain. Existing analgesics can be classified into at least two categories, non-steroidal anti-inflammatory drugs (NSAIDs), and narcotic analgesics. NSAIDs (e.g., aspirin) inhibit the synthesis of prostaglandin, thereby decreasing the sensitivity of nerve endings. NSAIDs are primarily used to relieve inflammatory pain and other kinds of dull pain. Narcotic analgesics (e.g., morphine) act on $\mu$-type opium receptors of the central nerve system, mainly in the thalamencephalon and cortex, to relieve sharp pain, as well as dull pain. Although widely used to treat pain, e.g., in late stage cancer patients, and post-operative patients, narcotic analgesics are highly addictive and are associated with severe withdrawal symptoms. Their dosage has to be increased continuously to sustain their analgesic effects. Further narcotic analgesics have little if any therapeutic value for pain caused by neurotrosis.

SUMMARY

The invention is based, in part, on the discovery that purified HWAP-I polypeptide of the Chinese bird spider, *Selenocosmia huwena,* is a very effective analgesic. Accordingly, the invention features a method of reducing perceived pain in a subject. The method includes administering to the subject an effective amount of a purified polypeptide having an amino acid sequence at least 70%, 80%, 90%, 92%, or 95% identical to SEQ ID NO:1. The purified polypeptide can be HWAP-I which has the amino acid sequence of SEQ ID NO:1. The polypeptide can be administered as an epidural or as a parenteral solution. In addition, the purified polypeptide can be applied locally (e.g., by injection or topical application). The purified polypeptide can be formulated as a pharmaceutical composition, e.g., with a pharmaceutically acceptable carrier, in a sterile solution, e.g., a sterile saline solution.

In another aspect, the invention features a method of inhibiting calcium channel activity in a subject. The method includes administering to the subject an effective amount of a purified polypeptide having an amino acid sequence at least 70%, 80%, 90%, 92%, or 95% identical to SEQ ID NO:1. The purified polypeptide can be HWAP-I which has the amino acid sequence of SEQ ID NO:1. The polypeptide can be administered as an epidural or as a parenteral solution. In addition, the purified polypeptide can be applied locally (e.g., by injection or topical application). The purified polypeptide can be formulated as a pharmaceutical composition, e.g., with a pharmaceutically acceptable carrier, in a sterile solution, e.g., a sterile saline solution. The method can reduce the amount of calcium channel activity in a local area of a subject, e.g., at least 10%, 20%, 30%, 40%, 50%, 70% or more using an assay described herein.

In another aspect, the invention features an article of manufacture. The article includes: i) a container; ii) a purified polypeptide, disposed in the container, and having an amino acid sequence at least 70%, 80%, 90%, 92%, or 95% identical to SEQ ID NO:1; and iii) a label, disposed on the container and having instructions for administration of the purified polypeptide. The purified polypeptide can be HWAP-I which has the amino acid sequence of SEQ ID NO:1. The purified polypeptide can be formulated as a pharmaceutical composition, e.g., with a pharmaceutically acceptable carrier, in a sterile solution, e.g., a sterile saline solution. The instructions can provide directions for administration of the purified polypeptide to a subject, e.g., for epidural, intrathecal, parenteral, or local administration. The instructions can indicate that the treatment is relief of pain in a subject or to reduce calcium channel activity in a subject.

In still another aspect, the invention features isolated nucleic acids that include a sequence at least 70%, 80%, 85%, 90%, 92%, 95% identical to SEQ ID NO:2 or 3. The isolated nucleic acid can be identical to SEQ ID NO:2 or 3. Further, the isolated nucleic acid can have a strand that hybridizes under high stringency conditions to a single-stranded probe, the sequence of which consists of SEQ ID NO:2 or 3 or the complement of SEQ ID NO:2 or 3. Also included are nucleic acids further containing a heterologous promoter operably linked to the HWAP-I-related sequence. The heterologous promoter can be a prokaryotic or eukaryotic promoter, and/or, an inducible promoter. The invention further features a method of providing a calcium channel inhibitor. The method includes: providing cells having a heterologous nucleic acid sequence encoding a polypeptide having an amino acid sequence at least 70%, 80%, 90%, or 95% identical to SEQ ID NO:1 and optionally a heterologous promoter operably linked to the encoding sequence; culturing the cells in a medium; extracting the polypeptide from the cells or the medium to thereby provide a calcium channel inhibitor.

A "purified polypeptide", as used herein, refers to a polypeptide that has been separated from other proteins, lipids, and nucleic acids with which it is naturally associated. The polypeptide can constitutes at least 10%, 20% 50%, 70%, 80% or 95% of the purified preparation by dry weight.

An "isolated nucleic acid" is a nucleic acid the structure of which is not identical to that of any naturally occurring nucleic acid, or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones: e.g., as these occur in a DNA library such as a cDNA or genomic DNA library.

The "percent identity" of two amino acid sequences or of two nucleic acids is determined using the algorithm of Karlin and Altschul *Proc. Natl. Acad. Sci.* USA 87:2264–68, 1990, modified as in Karlin and Altschul *Proc. Natl. Acad.*

Sci. USA 90:5873–77, 1993. Such an algorithm is incorporated into the NBLAST and XBLAST programs (version 2.0) of Altschul, et al. *J. Mol. Biol.* 215:403–10, 1990. BLAST nucleotide searches can be performed with the NBLAST program, score=100, wordlength-12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17):3389–3402, 1997. When utilizing BLAST and Gapped BLAST programs, the default parameters of the respective programs (e.g., XBLAST and NBLAST) can be used. See resources of the National Center for Biotechnology Information (NCBI), Bethesda Md.

As used herein, the term "hybridizes under stringent conditions" refers to conditions for hybridization in 6× sodium chloride/sodium citrate (SSC) at about 45° C., followed by one or more washes in 0.2 ×SSC, 0.1% SDS at 50°–65° C.

The term "heterologous" refers to a polypeptide that is introduced into a context by artifice. A heterologous polypeptide can be identical to endogenous entity that is naturally present. In distinction from an endogenous entity, a heterologous polypeptide can have a polypeptide flanking it on at least one side that does not flank it in a naturally occurring polypeptide. Similarly, the term "hybrid" refers to a polypeptide which comprises amino acid sequences derived from either (i) at least two different naturally occurring sequences, and derivatives, variants, and multiple mutants thereof, or (ii) from an artificial sequence and a naturally occurring sequence, and a derivative, variant, or multiple mutant thereof.

The details of one or more embodiments of the invention are set forth in the accompanying drawings and the description below. Other features, objects, and advantages of the invention will be apparent from the description and drawings, and from the claims.

DETAILED DESCRIPTION

Pain is a symptom of a wide variety of ailments. Pain can be both chronic and acute. It can arise as a consequence of injuries, trauma, certain cancers, and the like. In addition, neuropathic pain can arise from a number of separate etiologies. Neuropathic pain may occur as a consequence of ophthalmic surgery, dental repair (root canal), burn injury, reflex sympathetic dystrophy, post-herpetic neuralgia, diabetic neuropathy, arthritis and the like. The inventors have discovered that HWAP-I and related polypeptides are useful agents for the treatment and relief of pain in subjects.

HWAP-I

The polypeptide sequence of *Selenocosmia Huwena* HWAP-I is: NH$_2$-Ala-Cys-Lys-Gly-Val-Phe-Asp-Ala-Cys-Thr-Pro-Gly-Lys-Asn-Glu-Cys -Cys-Pro-Asn-Arg-Val-Cys-Ser-Asp-Lys-His-Lys-Trp-Cys-Lys-Trp-Lys-Leu-COOH (SEQ ID NO:1). The naturally occurring nucleic acid sequence encoding HWAP-I is:
5'-GCATGCAAAGGGGTCTTCGATGCATGCACACCTG GAAAGAATGAGTGC TGTCCAAACCGTGTTTG- TAGTAAACACAAGTGGT GCAAATGGAAGCTG-3' (SEQ ID NO:2).

A preferred synthetic nucleic acid sequence encoding HWAP-I is:
5'-GCTTGCAAAGGTGTTTTCGACGCTTGCACCCCGG GTAAAAACGAGTGC TGCCCGAACCGT- GTTTGCTCTGACAAACATAAAT GGTGCAAATGGAAACTG-3' (SEQ ID NO:3)

HWAP-I Related Polypeptides

Polypeptides related to HWAP-I can be obtained by a number of methods. For example, HWAP-I related polypeptides can be purified from the venom of spiders, e.g., from the Theraphosidae family of arachnids, e.g., species of the genera Acanthoscurria (e.g., *Acanthoscurria gomesiana*), Aphonopelma (e.g., *Aphonopelma chalcodes,* Aphonopelma sp.), Brachypelma (e.g., *Brachypelma smithii*), Coremiocnemis (e.g., *Coremiocnemis validus,* Dugesiella (e.g., Dugesiella sp.), Eurypelma (e.g., *Eurypelma californicum*), Grammostola (e.g., *Grammostola spatulata,* Hysterocrates (e.g., *Hysterocrates gigas*), Scodra (e.g., *Scodra griseipes*), or Selenocosmia. The polypeptide can be extracted, e.g., following the method described below for extracting HWAP-I, and then sequenced, e.g., by Edman degradation. Synthetic oligonucleotides can be synthesized to produce a nucleic acid encoding the polypeptide.

Another method for obtaining related HWAP-I polypeptides is nucleic acid hybridization with oligonucleotides or nucleic acid fragments having the HWAP-I sequence, e.g., the natural sequence encoding HWAP-I polypeptide. For example, a library of arachnid genomic or cDNA clones can be hybridized under low stringency conditions with the probe nucleic acid. Stringency conditions are modulated to reduce background signal and increase signal from potential positives as is done routinely in the art (see, e.g., *Current Protocols in Molecular Biology,* John Wiley & Sons, N.Y. (1989), 6.3.1–6.3.6). Clones so identified can be sequenced to verify that they encode a polypeptide sequence related to HWAP-I.

Another hybridization-based method utilizes an amplification reaction (e.g., the polymerase chain reaction (PCR)). Oligonucleotides, e.g., degenerate oligonucleotides, are designed to hybridize to an HWAP-I sequence. The oligonucleotides are used as primers to amplify an HWAP-I-like sequence from template nucleic acid from an arachnid, e.g., a Theraphosidae species. The amplified fragment can be cloned and/or sequenced.

In another method, an HWAP-I-like sequence is identified from a sequence database, e.g., a protein or nucleic acid database using a sequence disclosed herein as a query. Sequence comparison programs can be used to compare and analyze the nucleotide or amino acid sequences. One such software package is the BLAST suite of programs from the National Center for Biotechnology Institute's (Altschul, et al., (1997) *Nuc. Acids Research* 25:3389–3402.). Synthetic oligonucleotides can be synthesized to produce a nucleic acid encoding the polypeptide.

Once a nucleic acid encoding a HWAP-I related polypeptide is obtained, the polypeptide itself can be characterized and used as an analgesic. For example, the encoding nucleic acid is cloned into an expression vector and the encoded polypeptide is purified as described for HWAP-I below.

A preparation of HWAP-I or a related polypeptide can be evaluated using analgesic tests on animals, e.g., the hot plate test, tail flick test, writhing test, paw pressure test, all electric stimulation test, tail withdrawal test, or formalin test (Roques et al. (1995) *Methods in Enzymology* 248:263–283). Animal models of pain response include, but are not limited to, axotomy, the cutting or severing of an axon; chronic constriction injury (CCI), a model of neuropathic pain which involves ligation of the sciatic nerve in rodents, e.g., rats; or intraplantar Freund's adjuvant injection as a model of arthritic pain. Other animal models of pain response are described in, e.g., *ILAR Journal* (1999) Volume 40, Number 3 (entire issue). In particular, the tests described below (see Examples) can be used.

Assays for HWAP-I

In addition, a preparation of HWAP-I or a related polypeptide can be evaluated for its ability to inhibit presynaptic activity or calcium channel function. These methods have been previously used to assay purified HWAP-I.

Assay for Inhibition of Presynaptic Activity. The preparation was applied to isolated nerve-synapse preparations of guinea pig ileum. The assay was done according to the procedure of Harry ((1964) *J. Pharm. Pharmacol.* 16:332–336) (see also, e.g., Liang et al. (2000) *Toxicon* 38:1237). 4 cm segments were dissected from the ileum of a guinea pig, in the region about 15 cm from the ileo-caecal junction. The segments were placed into a 10 ml water-jacketed glass bath equilibrated at 32° C. and containing Tyrode's solution (136.7 mM NaCl; 2.7 mM KCl; 1.82 mM $CaCl_2$; 1.19 mM $NaHCO_3$; 1.05 mM $MgCl_2$, 0.41 mM $NaH_2PO_4$ 5.6 mM glucose). 95% $O_2$ and 5% $CO_2$ were bubbled through the solution. Pulses of rectangular current, 0.05 ms in duration and of a strength of 25 V, were applied to the segments using platinum electrodes. The intraluminal electrode was connected to the anode. The contraction of the segments was recorded with a two-channel physiology recorder (Chengdu Instruments Model NO. LMS-2B). Prior to the assay, the segments were equilibrated in Tyrode's solution for 30 minutes. To determine the activity of a HWAP-I polypeptide preparation or a polypeptide of a related polypeptide, the preparation is added, e.g., while monitoring the twitch response of the ileum segment. An active HWAP-I preparation is able to inhibit the twitch response, e.g., at a concentration of about less than 100 $\mu$M, 10 $\mu$M, or 1 $\mu$M.

Another convenient assay is the mouse phrenic nerve-diaphragm assay (Liang (1997) *Science in China (Series C)* 40:449). The mouse phrenic nerve-diaphragm preparation was placed in a small plexiglas chamber and immersed in Tyrode's solution with 95% $O_2$ and 5% $CO_2$ bubbled through at 30 to 32° C. Electrical stimulation was applied to the phrenic nerve with a suction electrode or directly to the muscle. The electrical pulse was 0.2 Hz (supramaximal 0.2 ms, square wave). The twitch responses were transformed into electric signals by a mechanical-electric transducer, amplified, and recorded with a chart recorder. Application of native HWAP-I results in an inhibition of the indirect twitch response. At $1 \cdot 10^{-5}$ g/ml, native HWAP-I blocked neuromuscular transmission for 14.3±3.2 minutes.

Additional assays can be done with toad heart and the rat vas deferens (e.g., as described in Liang et al. (2000) *Toxicon* 38:1237).

$Ca^{2+}$ channel Inhibition Assay. HWAP-I is a potent inhibitor of the high-voltage-activated $Ca^{2+}$ channel expressed in prostaglandin $E_1$ differentiated NG108-15 cells (e.g., available from Shanghai Cell Institute). Cells were cultured in 90% Dulbecco's modified Eagle's medium (DMEM) with 10% newborn calf serum, hypoxanthine aminopterin thymidine supplement and penicillin-streptomycin. Cells were transferred to plates for electrophysiological experiments and cultured with 1% calf serum and 98% DMEM. Prostaglandin $E_1$ (10 $\mu$M) and 3-isobutyl-1-methylxanthine (50 $\mu$M) were added to the medium. Macroscopic $Ca^{2+}$ channel currents (filtered at 10 kHz, digitized at 3 kHz with a EPC-9 patch clamp amplifier, HEKA Electronics, Germany) were recorded at room temperature using $Ba^{2+}$ as the charge carrier. Cells were held at −40 mV potential and then depolarized to 0 mV. At 10 $\mu$M, HWAP-I was a potent inhibitor of the $Ca^{2+}$ current. Inhibition was dose dependent. The $EC_{50}$ for inhibition was approximately 100 nM ($EC_{50} \approx 100$ nM). HWAP-I is highly specific for this channel as the low-voltage-activated $Ca^{2+}$ channel was unaffected.

Methods of Obtaining HWAP-I Polypeptide

HWAP-I or an HWAP-I-related polypeptide can be obtained by the following non-limiting methods: (i) extraction from spider venom; (ii) solid-phase synthesis; and (iii) purification from an recombinant expression system.

Extraction from Spider Venom. HWAP-I was isolated from the venom of the Chinese bird spider *Selenocosmia huwena* by the method as follows. Adult female *Selenocosmia huwena* spiders were collected in the hilly area of Ningming country, Guangxi, China. The spiders were kept in wooden boxes covered with plastic net and given water daily. Cockroaches, small mice and small frogs were used to feed the spiders. The venom was obtained every 3–4 weeks by the following method. A spider was immobilized with a pair of tweezers. A bundle of flexible polyvinyl plastic tubing (2 mm i.d×45 mm), held by another pair of tweezers, was used to provoke the spider to grasp the tubing tightly, pierce the tubing with its fangs, and inject the venom inside. The process can be repeated, e.g., to ensure engagement of both fangs. The venom was removed from the tubing with a pipetman. The crude venom was lyophilized to obtain a dry white powder.

The powder was rehydrated with water and loaded onto a C4 reverse phase high performance liquid chromatography (HPLC) column (Waters Co., USA, Delta Pack C4-300A, 30×0.46 cm) equilibrated with 0.1% trichloroacetic acid (TCA). The column was eluted with a linear gradient of 0% to 70% acetonitrile with 0.1% TCA over the course of 120 minutes at a flow rate of 0.7 to 1.0 ml/min, and a temperature of 45° C. The major peak containing HWAP-I was identified and lyophilized. The sample was then further purified by ion-exchange chromatography on a WCX-1 ion-exchange high performance liquid chromatography (HPLC) column (Shim-pack, Japan, 5×0.4 cm) equilibrated in 20 mM sodium phosphate buffer (pH 6.6). The column was eluted with a linear gradient of 0% to 45% of 1M sodium acetate (pH 7.0) over the course of 30 minutes at a flow rate of about 0.8 ml/min. The second major peak detected by UV absorption at 220 nm corresponded to HWAP-I. The sample was desalted on a YWG-C18 column, and lyophilized. The sample was at least about 98% pure. It migrated as a single species on an SDS page gel and by IEF electrophoresis. Mass spectroscopy indicated that its molecular weight was 3749.3 Daltons, consistent with its predicted molecular weight of 3750 Daltons.

Solid Phase Synthesis. HWAP-I was prepared synthetically using Fmoc amino acid pentafluorophenyl esters on a standard laboratory solid phase synthesis station. The activation of a polyethylene glycol polystyrene resin and the general synthetic protocols were performed according to the procedure of Atherton et al. (1989) *Solid Phase Peptide Synthesis: A Practical Approach* Oxford University Press 47–122. The resin was activated by the reaction with 4-hydroxymethylphenoxyacetic acid-pentafluorophenyl ester and HOBt (1-Hydroxybenzotriazole). The first amino acid (the carboxy-terminal leucine) was coupled to the hydroxy groups of the activated resin by catalysis with dimethylaminopyridine (DMAP). Coupling yield was determined with the method of Sarin et al. (1981) *Analytical Biochemistry* 34:595. 200 mg Fmoc-Leucine-resin (0.23 mmol/g) was used as the starting material for the sequential synthesis of the amino acid sequence of HWAP-I. Fmoc amino acid pentafluorophenyl esters (3–4 times in excess)

dissolved in DMF (N,N-Dimethylformamide) were used in each coupling reaction to determine the extent of the coupling and the percentage of the uncoupled amine and to decide whether a second coupling was needed. During the synthesis the Trp3, Lys4, Glu19, Gly30 and Ala33 were coupled twice and the Val 3 was coupled for three times. After 32 steps of coupling the 33 residues peptide-resin was obtained and a sample of the peptide resin was removed for amino acid analysis.

A mixture tri-fluoroacetic acid-thioanisole-ethanedithiol-anisole (95:5:3:2; v/v/v/v) was used to cleave the polypeptide from the resin. The reaction was carried out under nitrogen in the dark for 4 hours. The resin was then filtered through a sintered glass funnel and washed 3 or 4 times with trifluoroacetic acid. The filtrate was collected and evaporated under vacuum. The cleaved and deprotected peptide product was washed with anhydrous ether and then evaporated under high vacuum.

The procedure of Saxena et al. (1970) *Biochemistry* 188:366 was used to correctly form the three disulfide bonds of HWAP-I. 28 mg of the synthesized product was dissolved in 2.5 ml Tris-HCl buffer (50 mmol/L, pH 6.2) containing 6 mol/L guanidine hydrochloride and 200 mmol/L DTT. The mixture was incubated for 40 min at 37° C. 1 mL of the above reaction solution was then added to 1 mL Tris-HCl buffer (1.5 mol/L, pH 8.0) containing 0.3 mmol/L oxidized glutathione and 3.0 mmol/L reduced glutathione. The mixture solution was then incubated at 4° C. and stirred with a magnetic stirrer for 5 days. The correctly oxidized peptide was finally purified by HPLC, e.g., as described above.

The procedure of Zhang et al. (1993) *J. Protein Chem.* 12:735 was used for the reduction and S-carboxymethylation of the synthesized peptide. The S-carboxylated peptide was purified by reverse phase HPLC, e.g., as described above.

Amino acid composition analysis was performed using a MilliGen Model 6600 ProSequencer. The synthetic and the native HWAP-I were dissolved in 0.5 mL of 20 mmol/L phosphate buffer (90% $H_2O$/10% $D_2O$) with a final concentration of 4 mmol/L.

The one dimensional nuclear magnetic resonance (1D-NMR) analysis was performed using a 500 MHz magnetic field on a Bruker AM-500 NMR spectrometer equipped with an Aspect 3000 computer. 1H-NMR spectra were recorded at 27° C. 36000 data points were acquired (128 scans per increment). The spectral width was 6494 Hz (12.987 ppm). Solvent suppression was carried out by using the presaturation method.

Recombinant Expression. The HWAP-I gene was constructed using two synthetic oligonucleotides that were synthesized using a Beckman Oligo 1000 DNA synthesizer (Applied Biosystem). The sequence of the two 108 mers are as follows:

5'-gatccgcttgcaaaggtgttttcgacgcttgcaccccgggtaaaaacgagtgct gcccgaaccgtgtttgctctgacaaacat aaatggtgcaaatggaaactgtgag-3'(Oligo 108A, SEQ ID NO:4); and 5'-aattctcacagtttccatttgcaccatttatgtttgtcagcgcaaacacggttcggg cagcactcgttttacccggggtgc aagcgtcgaaaacacctttgcaagcg-3 (Oligo 108B, SEQ ID NO:5).

The codon usage was optimized to obtain a high level of expression in *E. coli*. After confirmation of the sequence of the synthetic gene by dideoxy sequencing with an ABI 376 sequencer, the oligonucleotide cassette was ligated into pGEX-KT (Pharmacia, GST gene fusion vector. The recombinant plasmid was named pGH. The resulting construct includes nucleic acid sequence encoding glutathione-S-transferase (GST) and a thrombin cleavage site that separates the GST moiety from the HWAP-I coding sequences.

*E. coli* DH 5α harboring pGH were cultured and induced with IPTG (Isopropyl β-D-1-thiogalactopyranoside). In brief, bacteria were grown to $O.D_{550}$ nm ≈1.0–1.5 and then induced with 0.1 mM IPTG for 4 h at 37° C. Cells were harvested at 4000 g for 10 min, washed once with PBS, then suspended in lysis buffer consisting 1% Triton X-100, PBS, 2 mM EDTA and the protease inhibitor phenylmethanesulfonyl fluoride (1 mM) and incubated with 1 mg/ml lysozyme for 30 min. After digestion of DNA with DNase I, the lysate was centrifuged at 27,000 g for 30 min. Purification of the fusion protein (GST-HWAP-I) was achieved in a one-step procedure using affinity chromatography with glutathione-sepharose 4B under the conditions as described (Smith and Corcoran, 1990). The GST-HWAP-I was eluted with 5 mM GSH (reduced L-Glutathione), 50 mM Tris-HCl, pH 8.0. The eluate containing GST-HWAP-I was cleaved with thrombin, and rHWAP-I was purified from the cleavage mixture using size-exclusion HPLC on a Shimpac Diol-150 7.9×250 mm column. The column was eluted with 0.2 M $NH_4AC$, pH 6.0, at a flow rate of 0.6 ml/min. The rHWAP-I containing fraction was further purified with reverse-phase HPLC in a Vydac 4.6×250 mm C4 column. The column was eluted with a linear gradient of 30–65% acetonitrile containing 0.1% TFA at a flow rate of 1.0 ml/min.

The amino acid sequence of the purified rHWAP-I was analyzed using the method described by Liang and Laursen (1990) *Analytical Biochemistry* 188:366. Briefly, Edman degradation was performed on a MilliGen/Biosearch Model 6600 proSequencer using prepacked aminophenyl glass beads capillary column for immobilization and sequencing. rHWAP-I has an additional amino-terminal dipeptide, G-S, as a result of the thrombin cleavage sequence. Native HWAP-I was used as control for analyses. Mass spectrometry analysis of the rHWAP-I was performed using a MALDI-TOF mass spectrometer (Micromass Corp).

rHWAP-I was dissolved to a final concentration 1 mg/ml in a solution consisting of 0.1 M Tris-HCl pH 8.0, 6 M guanidine HCl, 2 mM EDTA, 100 mM DTT. The reduction was performed for 2 hours at room temperature. For renaturation, the solution system consisted of 0.1 M Tris-HCl pH 8.0, 1 mM EDTA and 4 mM GSSG (oxidized L-glutathione) was formed gradually in reduced peptide solution diluted 100 times. The final concentration of guanidine HCl was 1 M. The sample was stirred slowly for 24 hours at 4° C. Renatured rHWAP-I was purified further by reverse-phase HPLC on a Vydac 2.1×150 mm $C_{18}$ column. Elution was performed with a linear gradient of 0–37% acetonitrile containing 0.1% TFA at a flow rate of 0.6 ml/min. All the HPLC reactions were performed using a Waters 2010 HPLC separation system with a 990-model UV detector.

rHWAP-I can be reduced and re-oxidized following the procedures described above in order to obtain high specific activities.

Re-oxidized rHWAP-I had the same efficacy as native HWAP-I (e.g., purified from venom) in the mouse phrenic nerve-diaphragm assay for inhibition of neuromuscular transmission. At $1·10^{-5}$ g/ml, both rHWAP-I and native HWAP-I blocked neuromuscular transmission for similar durations (14.3±3.2 minutes for nature HWAP-I; 14.9±4.3 minutes for rHWAP-I).

Formulation

A composition containing an effective amount of HWAP-I can be administered to a subject requiring treatment. The composition can be administered parenterally, intravenously, topically, orally, buccally, nasally, rectally, subcutaneously, intramuscularly, or intraperitoneally. In one implementation, the composition can be injected, e.g., into the cerebro-spinal fluid.

The composition of the treatment is formulated to be compatible with the route of administration. The composition can be formulated as a tablet, capsule, solution, powder, inhalant, lotion, tincture, troche, suppository, or transdermal patch. See, e.g., *Journal of Pharmaceutical Sciences*, (1963), 52:918 et seq.

A solution for parenteral, intradermal, or subcutaneous administration can include: a sterile diluent such as water, saline, glycerin, fixed oils, polyethylene glycols, propylene glycol, or other synthetic solvents; an antibacterial agents such as benzyl alcohol or methyl parabens; an antioxidant such as ascorbic acid or sodium bisulfite; a chelating agent; a buffering agent such as acetate or phosphate. The solution can be stored in ampoules, disposable syringes, or plastic or glass vials.

A formulation for injection or intravenous administration can include a carrier which is a solvent or a dispersion medium. Suitable carriers include water, physiological saline, bacteriostatic water, Cremophor EL™ (BASF, Parsippany, N.J.) phosphate buffered saline (PBS), ethanol, polyols (e.g., glycerol, glycol, propylene glycol, and the like), and mixtures thereof. These compositions must be sterile and fluid to allow injection. Fluidity can be maintained with a coating such as lecithin or a surfactant. Microbial contamination can be prevented by the inclusion of antibacterial and antifungal agents, such as parabens, chlorobutanol, phenol, ascorbic acid, and thimerosal. Sugars and polyalcohols, such as manitol, sorbitol, sodium chloride, can be used to maintain isotonicity in the composition.

Sterility can be insured by filter sterilization of the solution. Alternatively, the solution can be produced from components that were individually filter-sterilized. A filter-sterilized component can be vacuum dried or freeze dried to produce a sterile powder. Such a powder can be rehydrated prior to injection with a sterile carrier solution.

Oral compositions include tablets, capsules, troches, suspensions, and solutions. Such compositions can be fashioned with an inert diluent or an edible carrier. Capsules are made by combining an appropriate diluent with the compound and filling the capsule with the mixture. Common diluents are starches such as powdered cellulose, or sugars such as sucrose, fructose, or mannitol. Tablets are made by wet or dry granulation or by compression. In addition to the desired compound, compositions for tablets can include: a binder such as microcrystalline cellulose, or gelatin; an excipient such as a starch; a sugar (e.g., lactose, fructose, glucose, methylcellulose, ethylcellulose); a gum (e.g. gum tragacanth, acacia); a disintegrating agent (e.g., alginic acid, Primogel, or corn starch); a lubricant (e.g., magnesium stearate or Sterotes); a glidant (e.g., colloidal silicon dioxide); a sweetening agent (e.g., sucrose or saccharin); a flavoring agent (e.g., peppermint, methyl salicylate, or orange flavoring); or any compound of a similar nature. Biodegradable polymers such as poly-D,L-lactide-co-glycolide or polyglycolide, can be used as a matrix to delay the release of the composition (see e.g., U.S. Pat. Nos. 5,417,986, 4,675,381, and 4,450,150).

For administration by inhalation, the compounds are delivered in the form of an aerosol spray from pressured container or dispenser which contains a suitable propellant, e.g., a gas. Systemic administration can also be by transmucosal, e.g., with a nasal spray or suppository, or by transdermal means, e.g., as a salve, ointment, gel, or cream. Such modes of administration can use formulations containing detergents, bile salts, and fusidic acid derivatives.

Modes of Administration. Analgesia can be produced by epidural administration of the HWAP-I polypeptide. The polypeptide can be given by bolus injection, or by continuous infusion so as to prolog contact with the epidural region. The polypeptide can be infused for at least 3, 8, 12, or 24 hours. However, dosage and timing of administration can be modified according to the needs of the particular subject, e.g., within the framework of standard clinical protocols for treating pain. The polypeptide can also be delivered by intrathecal routes, and into the bloodstream. In addition, implantable or body-mountable pumps can be used to deliver the HWAP-I polypeptide at a controlled rate. U.S. Pat. No. 4,619,652 describes a body-mountable pump that can provide the polypeptide at a tonic flow rate or in periodic pulses. An injection site directly beneath the pump is delivers compound to the area of need, for example, to the perineural region. Alternatively, prolonged administration can be achieved by art-known depot or sustained release formulations.

Dosage. An appropriate dosage for treatment must be determined. Determination of the amount or dose required to treat an individual subject is routine to one skilled in the art, e.g., a physician, pharmacist, or researcher. First, the toxicity and therapeutic efficacy of the preparation of HWAP-I, is determined. Routine protocols are available for determining the $LD_{50}$ (the dose lethal to 50% of the population) and the $ED_{50}$ (the dose therapeutically effective in 50% of the population) in non-human animals. The therapeutic index is measured as the ratio of the $LD_{50}/ED_{50}$. Suitable ratios are greater than about 2, 5, 10, 50, or 100. Compounds, formulations, and methods of administration with high therapeutic indices can be determined, as such treatments have little toxicity at dosages which provide high efficacy. Compounds with toxic or undesirable side effects can be used, if means are available to deliver the compound to the affected tissue, e.g., the epidural space, spinal neurons and brainstem neurons, while minimizing damage to unaffected tissue, e.g., endothelial tissue.

In formulating a dosage range for use in humans, the effective dose of an HWAP-I preparation can be estimated from studies with laboratory animals, e.g., as described below. For example, therapeutically effective dosages in cell culture assays are about 0.1 nM, 1 nM, 10 nM, 100 nM, 1 $\mu$M, or 10 $\mu$M of inhibitor, and ranges between. A dose can be formulated in an animal in order to achieve a circulating plasma concentration of inhibitor that falls in this range. An exemplary dose produces a plasma concentration which exceeds the $IC_{50}$ (i.e., the concentration of the test compound which achieves a half-maximal inhibition of a symptom) as determined in cell culture assays. The circulating plasma concentration can be determined, for example, by obtaining a blood sample, and by analyzing the sample with high performance liquid chromatography or mass spectroscopy.

Alternatively, the dose can be estimated from tests in an animal model, as described below. Alleviation of symptoms is observed when rats receive HWAP-I polypeptide at a dose of at least about 10 $\mu$g/kg, 20 $\mu$g/kg, 40 $\mu$g/kg, 80 $\mu$g/kg, 120 $\mu$g/kg, 180 $\mu$g/kg, 240 $\mu$g/kg, 300 $\mu$g/kg, or 360 $\mu$g/kg. The interrelationship of dosages for animals and humans (based on milligrams per meter squared of body surface) is described by Freireich et al., *Cancer Chemother. Rep.* 1966, 50, 219. Body surface area may be approximately determined from height and weight of the patient. See, e.g., Scientific Tables, Geigy Pharmaceuticals, Ardley, N.Y., 1970, 537. An effective dose for treating human patients is estimated to be approximately at least 3 µg/kg, 30 µg/kg, 120 µg/kg, 180 µg/kg, 240 µg/kg, 300 µg/kg, or 500 µg/kg. The polypeptide can be administered with a frequency or continuously in order to maintain a local concentration effective to reduce pain in the subject. Depending on the method of administration, the appropriate dose can vary, e.g., from about 10 µg kg$^{-1}$ day$^{-1}$ to about 10 mg kg$^{-1}$ day$^{-1}$. The dose for a patient can be optimized while the patient is under care of a physician, pharmacist, or researcher. For example, a relatively low dose of the HWAP-I preparation can be administered initially. The patient can be monitored for symptoms and sensation of pain as described below. The dose can be increased until an appropriate response is obtained. In addition, the specific dose level for any particular subject can vary depending on the age, body weight, general health, gender, and diet of the subject, the time of administration, the route of administration, the rate of excretion, and other drugs provided in combination.

Uses

The HWAP-I polypeptide can be administered to a subject suffering from pain. The treatment can be part of a therapeutic or prophylactic protocol. The subject can be suffering from pain for any of a variety of reasons, e.g., due to a pain or a pain-associated disorder disclosed herein. For example, the subject can be a patient with pain elicited from tissue injury, e.g., inflammation, infection, ischemia; pain associated with musculoskeletal disorders, e.g., joint pain; tooth pain; headaches, e.g., migraine; pain associated with surgery; pain related to inflammation, e.g., irritable bowel syndrome; or chest pain. The subject can be a patient with complex regional pain syndrome (CRPS), reflex sympathetic dystrophy (RSD), causalgia, neuralgia, central pain and dysesthesia syndrome, carotidynia, neurogenic pain, refractory cervicobrachial pain syndrome, myofascial pain syndrome, craniomandibular pain dysfunction syndrome, chronic idiopathic pain syndrome, Costen's pain-dysfunction, acute chest pain syndrome, gynecologic pain syndrome, patellofemoral pain syndrome, anterior knee pain syndrome, recurrent abdominal pain in children, colic, low back pain syndrome, neuropathic pain, phantom pain from amputation, phantom tooth pain, or pain asymbolia. The subject can be a cancer patient, e.g., a patient with brain cancer, breast cancer, lung cancer, bone cancer, or prostrate cancer. Other examples of pain conditions include pain induced by parturition, or post-partum pain.

A skilled artisan can obtain and purify a HWAP-I polypeptide of the invention and utilize it to the fullest extent based on the guidance of the following specific examples, which are merely illustrative, and not limitative of the scope of the invention. All publications cited herein are incorporated in their entirety by reference.

EXAMPLE 1

In this example, the efficacy of HWVAP-I for pain relief was assessed in a rat model system. The mode of administration was epidural, a technique frequently used to relieve pain, e.g., for patients after surgery and late-stage cancer patients. This method provides for the efficient delivery of a concentrated active ingredient with reduced side effects.

HWAP-I was isolated and purified from the crude venom of Selenocosmia huwena as described. Its purity was determined to be 99.5% by HPLC and matrix assisted laser desorption ionisation time-of-flight mass spectrometry (MALDI-TOF).

Adult Sprague-Dawley rats were anesthetized with 2% sodium pentobarbital (40 mg/kg, ip.). The neck skin was cut to expose the occipital membrane. HWAP-I, formulated in normal saline, was administered by a PE-10 polyethylene tube (14 cm) inserted into the epidural space (depth of insert: 7 cm) to the site of intumescence at the rats' waist. The insertion position of the tube was confirmed by anatomization after the experiment.

Pain tolerance assays were performed 1–4 days after the operation. A healthy rat was put into a fixed canister with its tail drooping from the bottom of the vessel. There were three spots on the tail labeled for irradiation. The intensity of light was adjusted so that the tail flick latency (TFL) of rat was within 2–4 seconds. The average of TFLs determined three times before drug treatment was deemed the baseline pain threshold of the rat. HWAP-I was administered to the rat using the inserted tube. After 20 minutes, the pain threshold was determined. The analgesic effect ($A_E$) was calculated according the following formula:

$$A_E = \frac{T_P - T_B}{T_B} \cdot 100\% \qquad \text{(Eq. 1)}$$

wherein $T_P$ is the TLF post-drug treatment, and $T_B$ is the baseline pain threshold.

The upper limit of the increased rate of pain threshold was 200% in order to avoid hurting the skin of rat-tail, e.g.., when the baseline pain threshold was 3 seconds. Irradiation was stopped as soon as the TFL exceeded 9 seconds.

54 rats (160–220 g), of either gender, whose $T_B$ basic pain thresholds were within 3–4 seconds, were chosen and divided randomly into six groups of nine rats. The rats in each group were treated with HWAP-I at a dose of 120 µg/kg, 180 µg/kg, 240 µg/kg, 300 µg/kg, 360 µg/kg respectively and with normal saline in control group.

All the five dosages of HWAP-I had analgesic effects. The pain threshold of the rats was increased 50–70% in an hour under 180 µg/kg HWAP-I and the duration time was over 3 hours. The pain threshold was increased 100% in an hour under 360 µg/kg HWAP-I and the duration of pain relief extended 6 hours. No significant analgesic effect was observed in the control normal saline group. When the HWAP-I dosage was around 600 µg/kg, some rats began to exhibit adverse effects, e.g., ataxia in the quarters. Most could be restored to normal without sequela.

The analgesic effect of HWAP-I was also compared to morphine hydrochloride. The analgesic effect of morphine (200 µg/kg) reached its maximum, and then decreased quickly and to 50% within a single hour in contrast to the six hour duration of pain relief from HWAP-I.

EXAMPLE 2

The HWAP-I preparation was delivered to the subarachnoid space by injection. This delivery method can be used to relieve pain in patients after surgery and cancer patients in the later period.

The method was testing using the rat experimental system. After anesthesia, the neck skin of a rat was cut. The occcipital membrane was exposed and a hole with 1 mm diameter was made with #5 needle. HWAP-I formulated in normal saline was administered with a PE-10 polyethylene tube (14 cm) inserted into the subarachnoid space (depth of insert: 7 cm) to the site of intumescence at the rats' waist. The insertion position of the tube was later confirmed by anatomization after experiment.

Assays were performed in 1–3 days after the operation. 28 rats (130–230 g), of either gender, whose basic pain thresholds were within 2–4 seconds, were chosen and divided randomly into four groups of seven rats. The rats in each group were treated with HWAP-I at dosages of 0.6 μg/kg, 1.5 μg/kg, and 3.0 μg/kg respectively and with normal saline (using a volume of 30 μl) for the control group.

All the three dosages of HWAP-I had analgesic effects. At a dose of 1.5 μg/kg HWAP-I, the pain threshold was increased 40–50% in an hour for a duration of one hour. At a dose of 3.0 μg/kg HWAP-I, the pain threshold was increased 100% in an hour for a duration of over 3 hours. No significant analgesic effect was observed in the control normal saline group. When HWAP-I was administered at a dose of 8 μg/kg, the rats showed some adverse effects like becoming ataxic in the quarters. Most were restored to normal without sequela.

The analgesic effect of HWAP-I was also compared by morphine hydrochloride (5 μg/kg). The results indicated that the duration of the analgesic effect of HWAP-I was longer than that of morphine.

EXAMPLE 3

The pain model induced by formalin is useful for evaluating moderate and continuous pain in animals. In this model, formalin is injected into the hind limb of an animal. Then pain is monitored as two phases. The first phase reaction is an acute one lasting for 3–5 minutes. The subsequent second phase is a tetanus reaction lasting for 20–40 minutes.

The degree of pain is assigned to one of four levels from 0 to 3 according to the reaction of the injected limb of rabbits, among which in level 0, no significant difference could be observed. The intensity of pain is evaluated by the following formula:

$$P_e = \frac{T_1 + 2 \cdot T_2 + 3 \cdot T_3}{180} \quad \text{(Eq. 2)}$$

$T_1$, $T_2$, and $T_3$ stand for the duration of reaction in level 1, level 2 or level 3 respectively per 180 seconds. Pain levels were assessed as follows:

0—The injected limb touches the floor closely and supports the animal's weight. There is no difference between the animal's use of its two fore limbs and two hind limbs;

1—Although the injected limb touches the floor gently, it does not support the animal's weight. An obvious limp is observed during locomotion;

2—The injected limb is not used by the animal to touch any surface;

3—The animal licks, gnaws, or shakes its injected limb.

Healthy New Zealand rabbits (1.5–3.0 kg) of either gender were chosen. A catheter was surgically inserted into the epidural space of each rabbit for subsequent drug administration. Five to six hours after surgery, the rabbits were treated and evaluated.

Rabbits were divided into four groups. (1) Control group: 13 rabbits were injected with only formalin in one of their hind limbs without any other treatment. (2) Normal saline control group: 8 rabbits were treated with 500 μl normal saline through the catheter inserted into epidural space. These animals were subjected to a formalin injection one hour after saline administration. (3) Morphine positive control group: 9 rabbits were treated with morphine hydrochloride (250 μg/kg) through the catheter. These animals were subjected to a formalin injection 30 minutes after morphine administration. (4) Treated group: This group was divided into two sub-groups. 28 rabbits were treated with 25–200 μg/kg HWAP-I through the catheter and then subjected to a formalin injection after one hour. These rabbits were used to monitor the effect of varying HWAP-I dosage. 25 rabbits were treated with 100 μg/kg HWAP-I through the catheter and then subjected to a formalin injection after a designated time, between 0.5–5 hours. These rabbits were used to monitor the duration of analgesia provided by HWAP-I.

These experiments indicated that HWAP-I (25–200 μg/kg) had a potent and robust analgesic effect in this pain model. The analgesic effects were most pronounced on the second phase in comparison to the first phase. Under the concentrations used, no obvious toxic side effects were observed. The duration of the analgesic effect as admnimistered by epidural was 5–6 hours.

EXAMPLE 4

A purified preparation of HWAP-I is formulated in sterile normal saline and stored in aliquots, e.g., 4 mg aliquots. The aliquots are lyophilized, e.g., in ampules, for later use for injection. Before used, an ampoule of 4 mg HWAP-I is dissolved in 2 ml sterile water, and then administered by injection into the vertebral canal, vein or muscle or by epidural, intrathecal administration. This regime can be used specifically as follows:

1) For patients with cancer or AIDS in later period, the HWAP-I formulation is administered through vertebral canal or vein.

2) For patients with severe chronic pain (e.g., resulting from pathological changes in spinal tissue, osteoarticulation, vessel and nerve damage), the HWAP-I formulation is administered for an extended period of time for pain relief.

3) For patients prior or after surgery and patients in parturition: the HWAP-I formulation can be administered prior to and after the event in order to relieve pain (e.g., post-surgical pain, and/or pain induced by childbirth).

EXAMPLE 5

HWAP-I can be formulated in liposome microcapsules (see, e.g., U.S. Pat. No. 4,900,550). Such microcapsules are effective medicinal carriers. The liposome envelops a refined powder of HWAP-I in a lipid bilayer.

The preparation of analgesic can be taken orally, e.g., by patients with rheumatic arthritis, morbus senilis, migraines and/or chronic headaches (e.g., due to neurosis); and by patients suffering from cervico-omathralgia, lumbo-skelalgia and acrodynia caused by diabetes.

EXAMPLE 6

HWAP-I can be formulated as a tooth drops analgesic. The refined powder of lyophilized HWAP-I is dissolved in a solvent (such as sterile distill water) and packaged as a tooth drop analgesic, which can be used to alleviate pain induced by toothaches and endodontitis.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method of reducing perceived pain in a subject, the method comprising: administering to the subject an amount of a purified polypeptide comprising SEQ ID NO:1, wherein the amount of the polypeptide and conditions are effective to reduce perceived pain.

2. The method of claim 1 wherein the effective amount is administered by injection.

3. The method of claim 2 wherein the effective amount is administered as a single bolus injection.

4. The method of claim 2 wherein the effective amount is administered as a an epidural injection.

5. The method of claim 4 wherein the effective amount is administered by continuous infusion.

6. The method of claim 1 wherein the effective amount is at least 3 micrograms per kilogram.

7. The method of claim 6 wherein the effective amount is at least 30 micrograms per kilogram.

8. The method of claim 7 wherein the effective amount is at least 120 micrograms per kilogram.

9. A method of inhibiting calcium channel activity in a subject, the method comprising administering to the subject an effective amount of a purified polypeptide comprising SEQ ID NO:1 to thereby inhibit activity of a calcium channel in the subject.

10. The method of claim 9 wherein the effective amount is administered by injection.

11. The method of claim 10 wherein the effective amount is administered as a an epidural injection.

12. A method of inhibiting calcium channel activity in a subject, the method comprising administering to the subject an effective amount of a purified polypeptide to thereby inhibit activity of a calcium channel in the subject, wherein the polypeptide comprises an amino acid sequence encoded by a nucleic acid that hybridizes under stringency conditions (6× sodium chloride/sodium citrate (SSC) at about 45° C.) to the nucleic acid of SEQ ID NO:2 or a complement thereof, is structured by three disulfide bonds, and blocks neuromuscular transmission in a mouse phrenic nerve diaphragm assay.

13. A pharmaceutical composition comprising a purified polypeptide comprising SEQ ID NO:1 and a pharmaceutically acceptable carrier.

14. The composition of claim 13 wherein the composition is in an injectable form.

15. An article of manufacture comprising:

i) a container;

ii) a purified polypeptide, disposed in the container, and comprising SEQ ID NO:1; and iii) a label, disposed on the container and having instructions for administration of the purified polypeptide.

16. The article of manufacture of claim 15, wherein the instructions indicate administration for pain relief.

17. The article of manufacture of claim 15, wherein the purified polypeptide is formulated with a pharmaceutically acceptable carrier.

18. A pharmaceutical composition comprising (1) a purified polypeptide that comprises an amino acid sequence that can be encoded by a nucleic acid that hybridizes under stringency condition (6× sodium chloride/sodium citrate (SSC) at about 45° C.) to the nucleic acid of SEQ ID NO:2 or a complement thereof, is structured by three disulfide bonds, and blocks neuromuscular transmission in a mouse phrenic nerve diaphragm assay, and (2) a pharmaceutically acceptable carrier.

* * * * *